(12) United States Patent
Arvin et al.

(10) Patent No.: US 9,347,147 B2
(45) Date of Patent: May 24, 2016

(54) METHOD AND APPARATUS FOR CONTROLLING AND MONITORING THE POTENTIAL

(75) Inventors: Charles L. Arvin, Poughkeepsie, NY (US); Harry Cox, Rifton, NY (US); Hariklia Deligianni, Tenafly, NJ (US); George J. Scott, Wappinger Falls, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 826 days.

(21) Appl. No.: 13/608,386

(22) Filed: Sep. 10, 2012

(65) Prior Publication Data
US 2013/0001198 A1  Jan. 3, 2013

Related U.S. Application Data

(63) Continuation of application No. 12/859,444, filed on Aug. 19, 2010, now Pat. No. 9,062,388.

(51) Int. Cl.
| | |
|---|---|
| *C03C 15/00* | (2006.01) |
| *C25D 17/00* | (2006.01) |
| *G01N 27/403* | (2006.01) |
| *G01N 27/404* | (2006.01) |

(Continued)

(52) U.S. Cl.
CPC .............. *C25D 17/007* (2013.01); *C25D 17/12* (2013.01); *C25D 21/12* (2013.01); *G01N 27/403* (2013.01); *G01N 27/404* (2013.01)

(58) Field of Classification Search
CPC ........ C25D 21/12; C25D 21/14; C25D 21/16; C25D 21/18; C25D 17/007; C25D 17/12; C23F 1/00; C23F 1/14; C23F 1/32; G01N 27/40; G01N 27/406

USPC ............ 216/83, 86, 103, 105, 84; 205/80, 81, 205/83

See application file for complete search history.

(56) References Cited

U.S. PATENT DOCUMENTS

| | | | | |
|---|---|---|---|---|
| 5,385,652 | A | * | 1/1995 | Wang et al. .................... 205/643 |
| 5,744,019 | A | * | 4/1998 | Ang ....................... C25D 17/12 |
| | | | | 118/500 |

(Continued)

OTHER PUBLICATIONS

U.S. Office Action dated Sep. 21, 2012 received in a related U.S. Patent Application, namely U.S. Appl. No. 12/859,444.

(Continued)

*Primary Examiner* — Lan Vinh
(74) *Attorney, Agent, or Firm* — Scully, Scott, Murphy & Presser, P.C.; Vazken Alexanian

(57) ABSTRACT

An electroplating apparatus including a reference electrode to control the potential during an electro-deposition process. The electroplating apparatus may include a bath containing a plating electrolyte and an anode present in a first portion of the bath containing the plating electrolyte. A cathode is present in a second portion of the bath containing the plating electrolyte. A reference electrode is present at a perimeter of the cathode. The electroplating apparatus also includes a control system to bias the cathode and the anode to provide a potential. A measuring system is provided in electrical communication with the reference electrode to measure the potential of the cathode. Methods of using the above described electroplating apparatus are also provided. Structures and method for electroless deposition are also provided.

16 Claims, 4 Drawing Sheets

(51) Int. Cl.
*C25D 17/12* (2006.01)
*C25D 21/12* (2006.01)

(56) References Cited

U.S. PATENT DOCUMENTS

| | | |
|---|---|---|
| 6,168,693 B1 | 1/2001 | Uzoh et al. |
| 6,270,647 B1 | 8/2001 | Graham et al. |
| 6,297,155 B1 | 10/2001 | Simpson et al. |
| 6,365,033 B1 | 4/2002 | Graham et al. |
| 6,508,924 B1 | 1/2003 | Gomez et al. |
| 6,562,204 B1 | 5/2003 | Mayer et al. |
| 6,669,833 B2 | 12/2003 | Kaja et al. |
| 7,022,212 B2 | 4/2006 | Zdunek |
| 7,189,318 B2 | 3/2007 | Wilson et al. |
| 7,449,098 B1 | 11/2008 | Mayer et al. |
| 7,704,352 B2 | 4/2010 | Lopatin et al. |
| 2002/0036146 A1* | 3/2002 | Akutsu et al. ............ 205/316 |
| 2004/0014240 A1* | 1/2004 | Takeguchi et al. ........ 436/518 |
| 2005/0230260 A1 | 10/2005 | Bleck et al. |
| 2006/0191784 A1 | 8/2006 | Hitzfeld et al. |
| 2006/0207874 A1 | 9/2006 | Miyata et al. |
| 2006/0228992 A1* | 10/2006 | Manens et al. ............ 451/5 |
| 2007/0289871 A1 | 12/2007 | Hafezi et al. |
| 2008/0179180 A1 | 7/2008 | McHugh et al. |
| 2009/0095634 A1 | 4/2009 | Makino et al. |
| 2010/0032303 A1* | 2/2010 | Reid et al. ............ 205/96 |
| 2010/0116672 A1 | 5/2010 | Mayer et al. |
| 2010/0240213 A1* | 9/2010 | Urano et al. ............ 438/652 |

OTHER PUBLICATIONS

S. Mehdizodeh, et al., "Optimization of Electrodeposit Uniformity by the Use of Auxiliary Electrodes", J. Electrochem Soc., vol. 137, No. 1, Jan. 1990, pp. 110-116.

W.M. Morgan, "Measuring Plating Uniformity", IBM Technical Disclosure Bulletin, vol. 38, No. 05, May 1995, pp. 127-129.

Catherine M. Cotell, et al., "Surface Engineering", ASM Handbook, vol. 5, pp. 165-329, Copyright 1994, Second printing date Feb. 1996.

Mordechay Schlesinger, Department of Physics, University of Windsor, "Electroplating" Electrochemisty Encyclopedia, Sep. 2002 (accessed Apr. 10, 2010) http://electrochem.cwru.edu/encycl/art-e01-electroplat.htm.

U.S. Office Action dated Apr. 18, 2013 issued in U.S. Appl. No. 12/859,444.

U.S. Office Action dated May 15, 2014 issued in related U.S. Appl. No. 12/859,444.

* cited by examiner

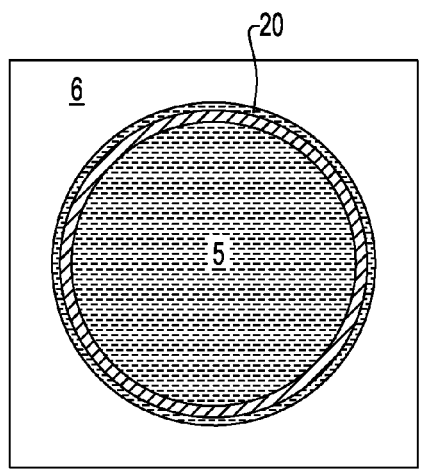
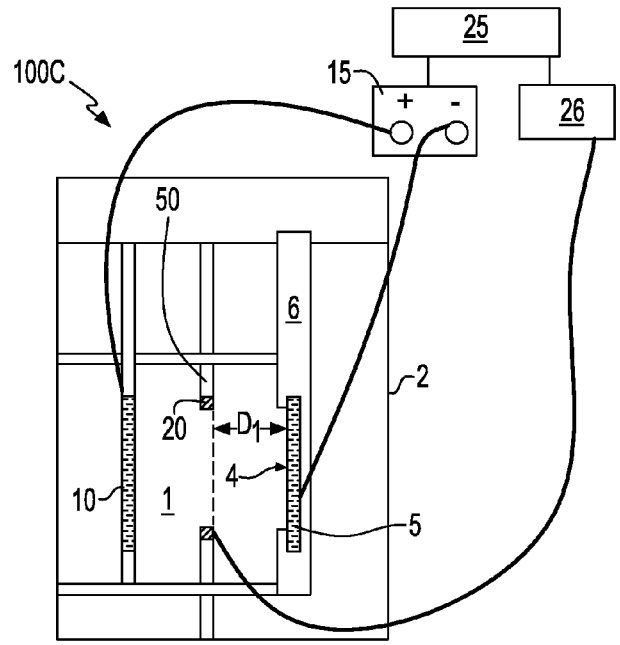
FIG. 3A  FIG. 3B
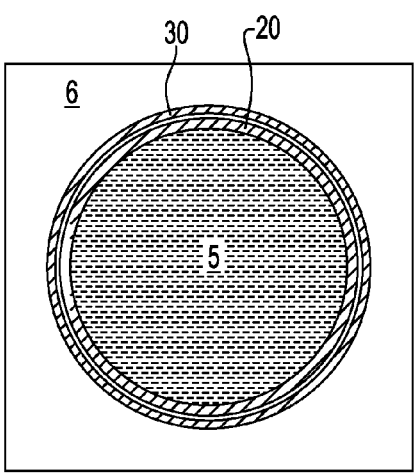
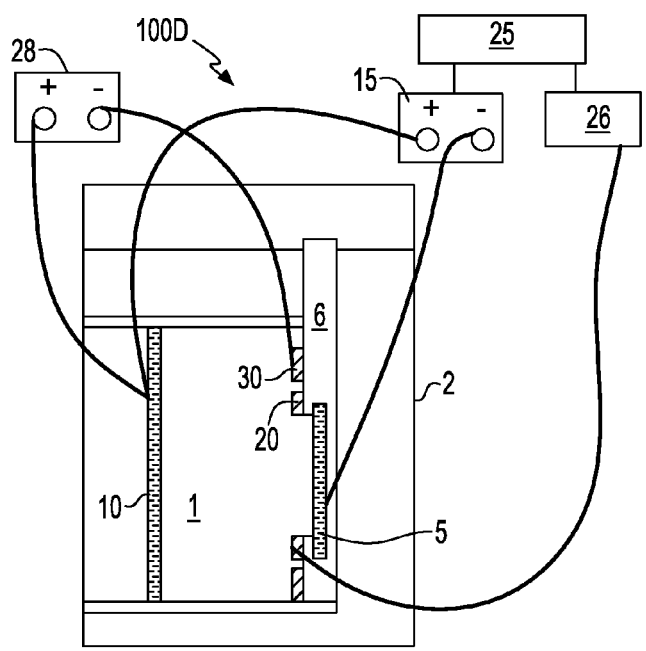
FIG. 4A  FIG. 4B

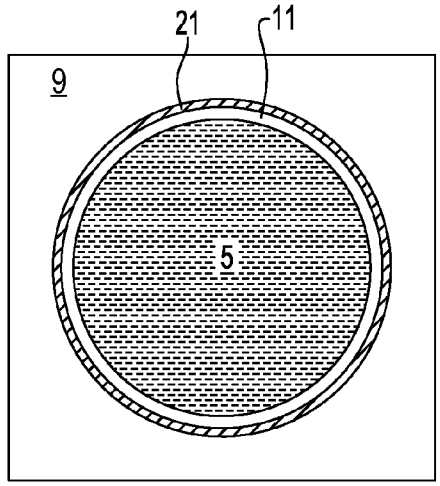
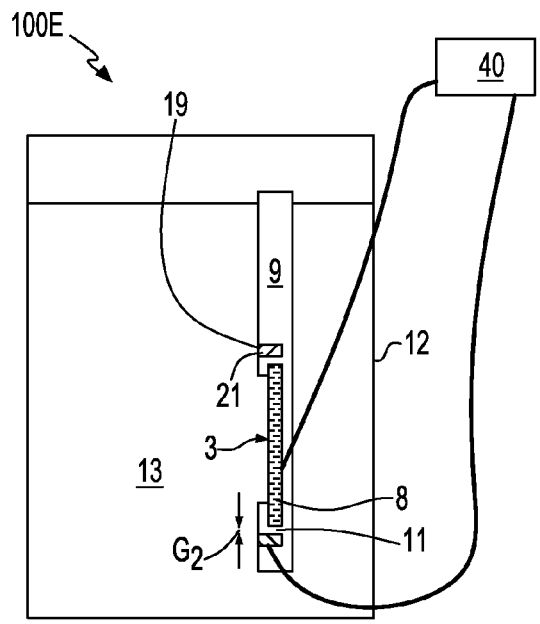
FIG. 5A  FIG. 5B
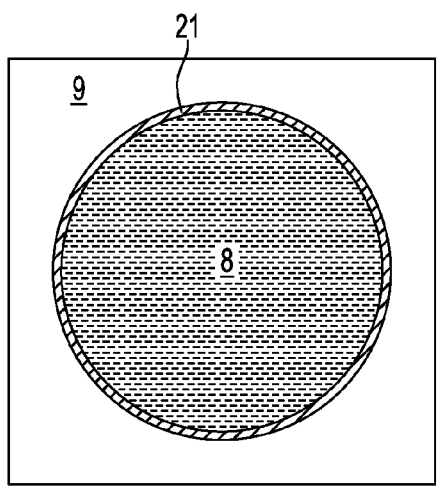
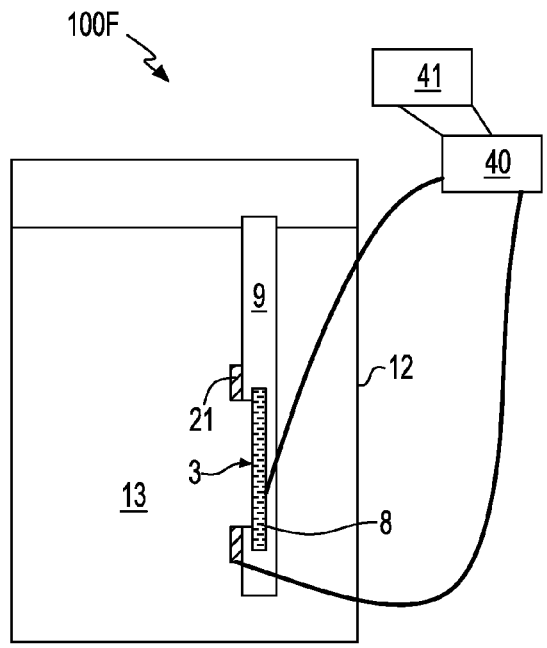
FIG. 6A  FIG. 6B

METHOD AND APPARATUS FOR CONTROLLING AND MONITORING THE POTENTIAL

CROSS REFERENCE TO RELATED APPLICATION

This application is a continuation of U.S. patent application Ser. No. 12/859,444, filed Aug. 19, 2010, the entire content and disclosure of which is incorporated herein by reference.

BACKGROUND

The present disclosure relates generally to electroplating. More particularly, in some embodiments, the present disclosure relates to controlling the potential of electroplating operations.

Microelectronic devices, such as semiconductor devices, imagers, displays, storage media, and micromechanical components, are generally fabricated on and/or in microfeature wafers using a number of processes that deposit and/or remove materials from the wafers. Electroplating is one such process that deposits conductive, magnetic or electrophoretic layers on the wafers. Electroplating processes, for example, are widely used to form small copper interconnects or other very small sub-micron features in trenches and/or holes (e.g., less than 90 nm damascene copper lines). Electropolishing is another process that removes material from a wafer. In both of these processes, an electrical current is passed between the wafer and one or more counter electrodes in a manner that deposits or removes material from a surface of the wafer. Another form of deposition is electroless deposition.

SUMMARY

An electroplating apparatus is provided that includes a reference electrode to control the potential during an electrodeposition process. In one embodiment, the electroplating apparatus includes a bath containing a plating electrolyte and an anode present in a first portion of the bath containing the plating electrolyte. A cathode is present in a second portion of the bath containing the plating electrolyte. A reference electrode is present at a perimeter of the cathode. The electroplating apparatus also includes a control system to bias the cathode and the anode to provide a potential. A measuring system is provided in electrical communication with the reference electrode to measure the potential of the cathode.

In another aspect, an electroless deposition apparatus is provided that includes a deposition substrate present in a bath including a plating electrolyte, a reference electrode present on a perimeter of the deposition substrate, and a measuring system in electrical communication with the reference electrode to measure the potential of the deposition substrate.

In another aspect, an electroplating method is provided in which a reference electrode is present about the perimeter of a working electrode and measures the potential of the working electrode during the electroplating process. In one embodiment, the electroplating method includes providing a bath containing a plating electrolyte, and positioning a counter electrode in a first portion of the plating electrolyte. A working electrode is positioned in a second portion of the plating electrolyte. A reference electrode is provided to measure the potential of the working electrode. The reference electrode is present around the perimeter of the working electrode. A bias is applied to the working electrode and the counter electrode to deposit metal from the plating electrolyte on the working electrode. Measurements taken by the reference electrode of the potential relative to the working electrode are used to determine the bias applied to the working electrode and the counter electrode for deposition.

In another aspect, an electroless deposition method is provided that includes providing a bath including a plating electrolyte having at least one metal compound, and positioning a reference electrode about the perimeter of a deposition substrate, wherein the reference electrode measures a potential of the deposition substrate. The deposition substrate and the reference electrode are positioned in the plating electrolyte to plate the deposition substrate with a metal from the at least one metal compound of the plating electrolyte. The potential of the deposition substrate is measured using the reference electrode. The deposition substrate is removed from the bath when the potential of the deposition substrate is equal to the open circuit potential for a plating composition on the deposition substrate.

In another aspect, an electroless etch method is provided that utilizes a reference electrode to measure the potential of the substrate being etched. In one embodiment, the electroless etch method includes providing a bath including an electrolyte, and positioning a reference electrode about the perimeter of an etch substrate, wherein the reference electrode measures the potential of the etch substrate. The etch substrate and the reference electrode are positioned in the electrolyte in which an oxidizing reaction removes at least one metal from the etch substrate. The potential of the etch substrate is measured using the reference electrode, wherein the etch substrate is removed from the bath when the potential of the etch substrate is equal to an open circuit potential.

BRIEF DESCRIPTION OF THE SEVERAL VIEWS OF THE DRAWINGS

The following detailed description, given by way of example and not intended to limit the invention solely thereto, will best be appreciated in conjunction with the accompanying drawings, wherein like reference numerals denote like elements and parts, in which:

FIG. 3A is a perspective view towards the deposition surface of a cathode system of an electroplating apparatus having a reference electrode that is separated from the holder that connects the cathode to the bath containing the plating electrolyte, wherein the reference electrode is present in the bath between the cathode and the anode, in accordance with one embodiment of the present disclosure.

FIG. 3B is a side cross-sectional view of an electroplating apparatus including the cathode system depicted in FIG. 3A.

FIG. 4A is a perspective view towards the plating surface of a cathode system of an electroplating apparatus having a reference electrode present at a perimeter of said cathode and further including a thief electrode, in accordance with one embodiment of the present disclosure.

FIG. 4B is a side cross-sectional view of an electroplating apparatus including the cathode system depicted in FIG. 4A.

FIG. 5A is a perspective view of a reference electrode incorporated into an electroless deposition apparatus, wherein the reference electrode is present at a perimeter of the deposition substrate, in accordance with one embodiment of the present disclosure.

FIG. 5B is a side-cross sectional view of an electroless deposition apparatus including the reference electrode depicted in FIG. 5A.

FIG. 6A is a perspective view of a reference electrode incorporated into an electroless deposition apparatus, wherein the reference electrode is connected to the holder of the substrate, wherein the reference electrode is overlapping a portion of the deposition substrate, in accordance with one embodiment of the present disclosure.

FIG. 6B is a side cross-sectional view of an electroless deposition apparatus including the reference electrode depicted in FIG. 6A.

DESCRIPTION OF THE PREFERRED EMBODIMENTS

Figure 1A:
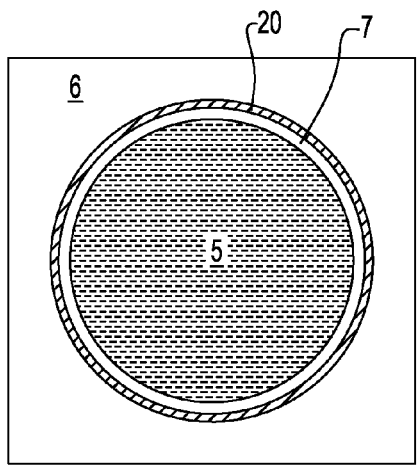
FIG. 1A is a perspective view towards the plating surface of a cathode system of an electroplating apparatus having a reference electrode present at a perimeter of the cathode, in accordance with one embodiment of the present disclosure.

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

The embodiments of the present disclosure relate to methods and structures for metal plating. FIGS. 1A-4B depict structures and methods for electroplating. Electroplating is the process of producing a coating, usually metallic, on a surface by the action of electric current. The deposition of a metallic coating onto an object is achieved by putting a negative charge on the object to be coated and immersing it into a solution, i.e., plating electrolyte 1, that contains a salt of a metal to be deposited on the electrode having the opposite charge as the metal ions. The metallic ions of the salt carry a positive charge and are thus attracted to the negatively charged electrode. When the metallic ions reach the negatively charged object (that is to be electroplated), it provides electrons to reduce the positively charged ions to metallic form. As used herein, the cathode 5 is a negatively charged electrode of the electroplating system, which is present in the bath containing the plating electrolyte 1. The cathode 5 typically provides the deposition surface. As used herein, the anode 10 is the positively charged electrode of the electroplating system, which is present in the bath 2 containing the plating electrolyte 1.

The anode 10 and cathode 5 in the bath 2 containing the plating electrolyte 1 are both connected to a power supply 15 of direct current (DC). The power supply provides an external supply of direct current (DC). The external supply of direct current may be a battery or a rectifier. The anode 10 is connected to the positive terminal of the power supply 15, and the cathode 5 (article to be plated) is connected to the negative terminal. When the power supply 15 is switched on, the metal at the anode 10 is oxidized from the zero valence state to form cations with a positive charge. These cations associate with the anions in the solution. The cations are reduced at the cathode to deposit in the metallic, zero valence state. For example, in one embodiment in which the plating electrolyte 1 is a copper containing acid solution, copper is oxidized at the anode to $Cu^{2+}$ by losing two electrons. The $Cu^{2+}$ associates with the anion $SO_4^{2-}$ in the solution to form copper sulfate. At the cathode 5, the $Cu^{2+}$ is reduced to metallic copper by gaining two electrons. The result is the effective transfer of copper from the source, i.e., anode 10 or plating electrolyte 1, to a plate covering the cathode 5.

In the embodiments depicted in FIGS. 1A-4B, a reference electrode 20 incorporated into the electroplating apparatus provides precise control of the potential during the electrodeposition process. The rate of electroplating is strongly dependent on current density, which is correlated with the applied voltage. Controlled-potential methods provide tighter control of the electroplating process than controlled-current methods. An apparatus for controlled-potential electroplating includes a reference electrode 20 placed near the surface to be plated, i.e., the cathode 5, which monitors its potential. As used herein, the reference electrode 5 is the electrode that measures the potential difference between itself and the working electrode but is not biased. Potential in traditional circuit design is measured between two points in an electrical circuit. However, in an electrochemical system, the electrochemical potential is referring to a combination of the voltage potential of a material and its surface potential at the metal/electrolyte interface caused by rearrangement of the atoms within the electrochemical double layer. The potential difference from the standard hydrogen electrode, which has a defined value of zero, is the potential that determines what electrochemical reaction will occur at that interface. By adjusting the power supply to keep the surface potential at the working electrode at the desired potential will insure the correct electrochemical reaction will occur. The potential difference is the difference between two points in a circuit, i.e., the anode 10 and the cathode 5, that is expressed in volts. This difference between the anode and cathode is not a measure of the potential at the working electrode interface. Rather, it is summation of all of the potential drops within the circuit as described below. By using a reference electrode, can the potential at the working electrode be known and controlled. The bias is the voltage, e.g., DC voltage, pulse or pulse reverse, applied to the anode 10 and the cathode 5 to control the electroplating operation.

Measuring and controlling the voltage (potential) across the bath 2 containing the plating electrolyte 1 using voltage values determined from the anode 5 and/or the cathode 10 are subject to considerable uncertainty. Interpreting the voltage as measured at the anode 5 and/or cathode 10 is complicated by the potential drop across the electrodes 5, 10 caused by surface kinetics and diffusion (concentration) potential drops across the cathode/anode/electrolyte interface. Such potential drops can be complicated functions of current, hydrodynamic effects, electrode size, shape, age, etc. as well as the processing history and the time during the electroplating process at which the voltage at the electrodes is measured.

To overcome the aforementioned disadvantages, in some embodiments of the present disclosure, a reference electrode 20 is positioned in the bath 2 containing the plating electrolyte 1, in which the reference electrode 20 is adjacent to, but is separated from the part to be coated, i.e., the cathode 5. In one embodiment, the reference electrode 20 is used to monitor and control the potential of the cathode 5. The reference electrode 20 measures the potential difference between itself and the surface of the cathode 5. Thus, in order to know the proper potential to control the working electrode, the reference electrode potential must either already be known as in the case of the saturated calomel electrode or determined as when using a quasi-reference electrode such as a metal wire relative to the standard hydrogen electrode. The potential measured by the reference electrode 20 differs from the potential measured across the power supply in a plating operation due to the charge-transfer potential drop across the surface of cathode 5 and the ohmic drop in solution between the cathode 5 and the reference electrode 20 due to diffusion overpotentials (concentration effects).

FIG. 1A depicts one embodiment of a cathode system of an electroplating apparatus having a reference electrode 20 present at a perimeter of the cathode 5. The cathode 5 may be composed of any electrically conductive material that is to be plated. As used herein, "conductive" denotes a room temperature conductivity of greater than about $10^{-8}(\Omega\text{-m})^{-1}$. Examples of suitable materials for the cathode 5 include elemental elements including, but not limited to Cu, Ag, Ni, Fe, Al, Ti, platinized Ti, SS 316, SS 304, Mo, W, Ru, Rh, Pd, In, Sn, Ta, Ir, Pt, Pb, Bi, Cr, Au, Zr, Nb and combinations and alloys thereof. The cathode 5 may also be composed of semiconductor materials, so long as the cathode 5 is conductive so that it may be biased to attract positively charged metal ions from the plating electrolyte 1. The cathode 5 may have any geometry to be plated. The cathode 5 may be circular or it may be multi-sided, e.g., rectangular. The cathode 5 is mounted to a holder 6 that is connected to the bath (not shown) in which the plating electrolyte is contained. The holder 6 is composed of a non-conductive material, such as a polymeric material, e.g., plastic or rubber, or glass material. The holder 6 is typically composed of the same material as the bath 2 that contains the plating electrolyte 1.

The reference electrode 20 carries essentially no current and is connected to a high impedance circuit and is, itself, unpolarized. The reference electrode 20 is present continuously about the perimeter of the cathode 5. By "continuously present" it is meant that there are no breaks in the body of the reference electrode 20. This does not exclude when the reference electrode 20 is composed of a mesh material. In one embodiment, the reference electrode 20 has the same geometric profile as the cathode 5. For example, in the embodiments, in which the cathode 5 is substantially concentric, the reference electrode 5 is substantially concentric. In the embodiment in which both the cathode 5 and the reference electrode 20 are both concentric, the reference electrode 20 represents a circular ring that surrounds the circular cathode 5.

The outline of the reference electrode 20 is consistent with the outline of the cathode 5 to ensure that the reference electrode 20 is in the closest proximity to the cathode 5, but is not in direct contact with the cathode 5. The term "direct contact" means that a first element, such as a first structure, and a second element, such as a second structure, are connected without any intermediary conducting, insulating or semiconductor layers at the interface of the two elements. In one embodiment, the reference electrode 20 is separated from the cathode 5 by an insulating material, such as an insulating spacer 7. In one embodiment, the insulating spacer 7 is an integrated component of the holder 6 for the cathode 5.

In the embodiment depicted in FIG. 1A, in which the reference electrode 20 and the cathode 5 are both substantially concentric, the reference electrode 20 is mounted to the holder 6, and is continuously radially present about the perimeter of the cathode 5.

The reference electrode 20 is separated from the cathode 5 by a radial gap G1. The radial gap G1 may be a dimension separating the cathode 5 from the reference electrode 20 ranging from 0.1 mm to 100 mm. In one embodiment, the radial gap G1 may be a dimension separating the cathode 5 from the reference electrode 20 ranging from 1 mm to 10 mm. In another embodiment, the radial gap G1 may be a dimension separating the cathode 5 from the reference electrode 20 ranging from 2 mm to 3 mm.

In one embodiment, the reference electrode 20 has a face 19 that is in contact with the plating electrolyte 1 that is offset from the plating surface 4 of the cathode 5. Although not depicted in FIG. 1A, the reference electrode 20 may have a face in contact with the plating electrolyte that is coplanar with a plating surface 4 of the cathode 5 (not shown).

Several different compositions are suitable for the reference electrode 20. A few examples for the composition of the reference electrode 20 are $Hg/Hg_2Cl_2$ (calomel), Ag/AgCl, $Hg/HgSO_4$, copper metal electrode ($Cu/Cu^{+2}$ couple), Pt wire, Ti wire, SS 316 ring and combinations thereof. Other examples of suitable materials for the reference electrode include, but are not limited to, Ag, Ni, Fe, Al, platinized Ti, SS 316, SS 304, Mo, W, Ru, Rh, Pd, In, Sn, Ta, Ir, Pt, Pb, Bi, Cr, Au, Zr, Nb and combinations and alloys thereof.

Figure 1B:
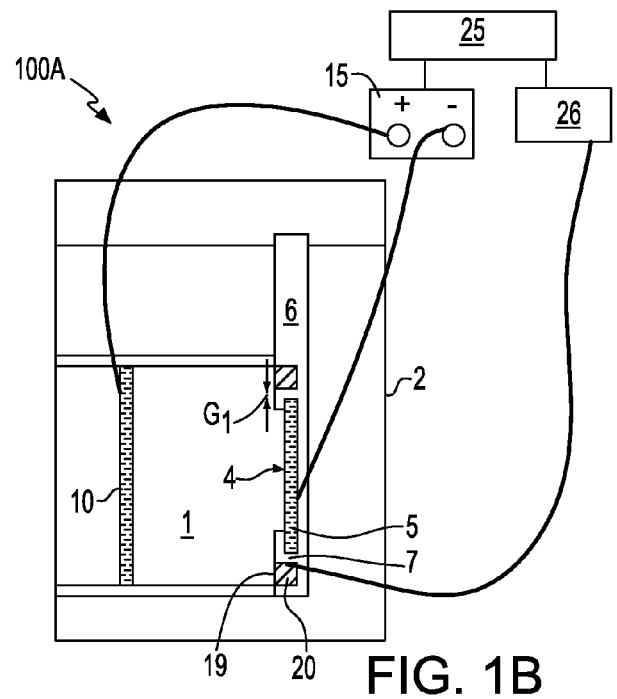
FIG. 1B is a side cross-sectional view of an electroplating apparatus including the cathode system depicted in FIG. 1A.

FIG. 1B depicts one embodiment of an electroplating apparatus 100A including the cathode 5 and reference electrode 20 that is depicted in FIG. 1A. In addition to the cathode system that is present in a second portion of the bath 2 containing the plating electrolyte 1, the electroplating apparatus 100A further includes an anode 10 that is present in a first portion of the bath 2 containing the plating electrolyte 1, a control system 25 to bias the cathode 5 and the anode 10 to provide a potential, and a measuring system 26 in electrical communication with the reference electrode 20 and the cathode 5. The measuring system 26 measures the potential relative to the cathode 5.

The bath 2 may be any vessel capable of holding a plating electrolyte, i.e., liquid solution. The bath 2 is typically composed of a non-conductive material, i.e., insulating material. As used herein, the term "insulating" means a material having a room temperature conductivity of less than about $10^{-10}(\Omega\text{-m})^{-1}$. Examples of materials for the bath 2 include glass, rubber, plastic or Koroseal™. Although, the bath 2 is typically a polymer, embodiments have been contemplated, in which low carbon steel is used for the bath 2.

The plating electrolyte 1 may be any electrolyte used for electroplating. For copper plating, the plating electrolyte 1 may be an alkaline plating bath, a dilute cyanide bath, Rochelle cyanide bath, sodium cyanide bath, potassium cyanide bath, alkaline noncyanide copper plating bath, or pyrophosphate bath or combination thereof. In the embodiments, in which copper is being plated onto the cathode 5, the plating electrolyte 1 may include, but is not limited to, copper cyanide, sodium cyanide, sodium carbonate, sodium hydroxide, Rochelle salt, potassium hydroxide, copper sulfate, sulfuric acid, copper fluoborate and combinations thereof.

In another embodiment, to plate chromium, the plating electrolyte 1 may be chromic acid in combination with a catalyst, such as sulfate. In another embodiment, to plate with nickel, the plating electrolyte 1 composition may include at least one of nickel sulfate, nickel sulfamate, nickel chloride, and boric acid. In yet another embodiment, to plate cadmium, the plating electrolyte 1 composition may be a cyanide bath or a non-cyanide bath. One example of a cyanide bath for plating cadmium includes at least one of cadmium oxide, cadmium metal, sodium cyanide, sodium hydroxide, and sodium carbonate. One example of a non-cyanide bath for plating cadmium includes at least one of ammonium chloride, ammonium fluobarate, ammonium sulfate, boric acid, cadmium, cadmium fluobarate, cadmium oxide, and sulfuric acid.

In a further embodiment, to plate with zinc, the plating electrolyte 1 composition may be a cyanide zinc bath or an alkaline noncyanide bath. In one example, a cyanide zinc bath is composed of at least one of zinc cyanide, sodium cyanide, sodium hydroxide, sodium carbonate, and sodium polysulfide. In one example, a noncyanide bath for plating nickel includes zinc oxide and sodium hydroxide. In yet another embodiment, the plating electrolyte 1 may also provide an indium plating. An indium plating may be provided by an indium fluoroborate plating bath composed of indium flouroborate, boric acid and ammonium fluoroborate. In another example, the indium plating may be provided by an indium sulfamate plating bath comprising indium sulfamate, sodium sulfamate, sodium chloride, dextrose and triethanolamine. Indium-lead fluobarate and indium-lead sulfamate plating baths are also possible.

Tin may be deposited from a plating electrolyte 1 that is composed of alkaline or acid baths. One example of an alkaline bath suitable for a plating electrolyte 1 that provides tin is composed of potassium stannate, sodium stannante, potassium hydroxide and tin metal. One example of an acid bath, i.e., sulfate (acidic) tin plating electrolyte, suitable for a plating electrolyte 1 that provides tin is composed of stannous sulfate, tin metal (as sulfate), free sulfuric acid, phenolsulfonic acid, β-naphthol, and gelatine.

Lead may be deposited from a plating electroltye 1 that is composed of fluobarate baths, fluosilicate baths, sulfamate baths and methane sulfonic acid baths. In one example, in which the plating electrolyte 1 is a fluobarate bath, the plating electrolyte 1 is composed of basic lead carbonate, hydrofluoric acid, boric acid and glue.

Silver may be deposited from a plating electrolyte 1 that is composed of a cyanide based solution composed of silver (as $KAg(CN)_2$, g/L (oz/gal)), potassium cyanide, and potassium carbonate. Non-cyanide solutions for electroplating silver include those based on simple salts such as nitride, fluobarate, and fluosilicite; inorganic complexes, such as iodide, thiocyanate, thiosulfate, pyrophosphate, and trimetaphosphate; and organic complexes, such as succiniumide, lactate and thiourea.

In another embodiment, the plating electrolyte 1 may be used to plate, i.e., deposit, gold on the cathode 5. A plating electrolyte 1 for depositing gold includes a source of gold, a complexing agent, and a conducting salt to help carry the current. The plating electrolyte for gold may also include an additive for color and hardness. In one example, the plating electrolyte for gold comprises gold as potassium gold cyanide, free potassium cyanide, dipotassium phosphate, sodium hydroxide, sodium carbonate, nickel as potassium nickel cyanide, and silver as potassium silver cyanide.

It is noted that the above-described compositions for the plating electrolyte 1 are included for illustrative purposes only, and are not intended to limit the disclosure. Other plating electrolytes have also been contemplated and are within the scope of the present disclosure. For example, the plating electrolyte 1 may also deposit palladium, ruthenium, rhodium, osmium, iridium and platinum.

Still referring to FIG. 1B, the anode 10 may be positioned within the bath 2 containing the plating electrolyte 1 and separated from the cathode 5. The anode 10 may be composed of a material to replenish the plating electrolyte 1 during the electroplating process. When forming copper plating, the anodes 10 may be composed of copper or iron. The copper may be cast copper, rolled copper, high purity copper, oxygen free copper and phosphorized copper. When forming a nickel plating, the anodes 10 may be composed of nickel. The anodes 10 for plating cadmium may be composed of a majority of cadmium, i.e., greater than 99% cadmium, alloyed with lead, iron, copper, arsenic and/or zinc. The anodes 10 for plating zinc may be composed of a majority of zinc, e.g., 99% zinc, alloyed with lead, cadmium, iron and copper. Anodes 10 for tin deposition are typically composed of tin. Anodes 10 for lead electroplating include lead and iron. Anodes 10 for silver electroplating may be composed of silver or stainless steel.

The electroplating apparatus 8 further comprises a control system 25 to bias the cathode 5 and the anode 10. The control system 25 is in electrical communication with the power supply 26 and each of the cathode 5 and the anode 10. The power supply 15 may be a direct current (DC) power supply, e.g., a battery, pulsed power supply, pulse reverse or the power supply 15 may be an alternating current (AC) employed in combination with a rectifier. The positive terminal of the power supply 15 is electrically connected to the anode 10 and the negative terminal of the power supply 15 is electrically connected to the cathode 5. In one embodiment, a measuring system 26, such as a voltmeter, is electrically connected to the cathode 5 and the reference electrode 20 to provide a measurement of the potential of the cathode 5. The value for the potential of the cathode 5 that is measured by the measuring system 26 is read by the control system 25, which then adjusts the power supply 15 to provide the proper bias to the cathode 5 and the anode 20. In one embodiment, the control system 25 is a proportional-integral-derivative controller (PID controller).

The control system 25 may control the voltage and the current density that is applied to the cathode 5 and the anode 10. In one embodiment, in which the metal to be plated is copper, the control system 25 dictates that the power supply 15 provide a substantially constant cathodic DC voltage having a value ranging from −5 mV to −100 mV with respect to the reference electrode 20 for a duration ranging from 0.5 seconds to 5 seconds. In another embodiment, in which the metal to be plated is copper, the control system 25 dictates that the power supply 15 provide a pulsed cathodic voltage having a value ranging from −10 mV to −500 mV with respect to the reference electrode 20, having a waveform period ranging from 0.1 ms to 10 ms for a duration of about 0.5 seconds to about 5 seconds.

Figure 2A:
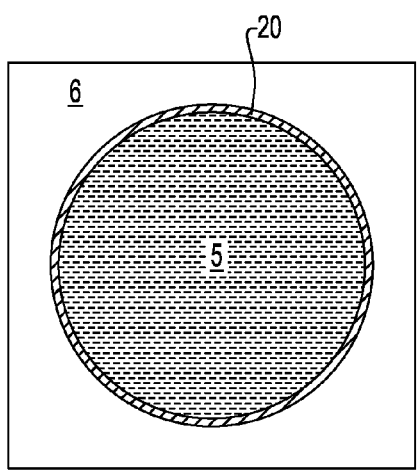
FIG. 2A is a perspective view towards the plating surface of a cathode system of an electroplating apparatus having a reference electrode connected to the holder that connects the cathode to the bath containing the plating electrolyte, wherein the reference electrode is overlapping a portion of the cathode, in accordance with one embodiment of the present disclosure.
Figure 2B:
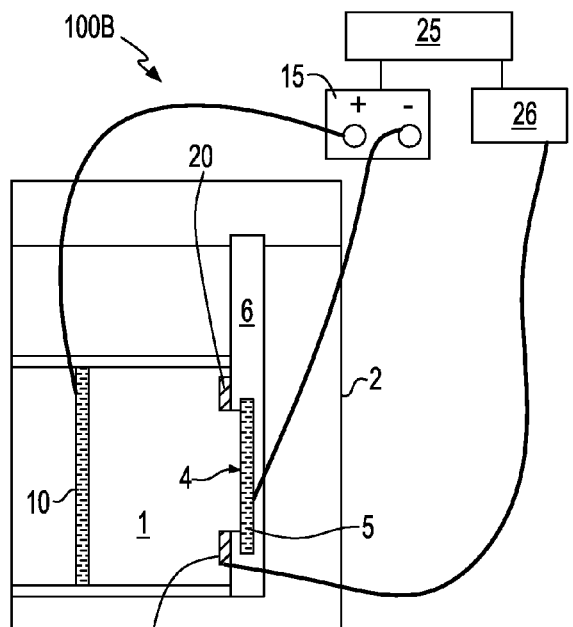
FIG. 2B is a side cross-sectional view of an electroplating apparatus including the cathode system depicted in FIG. 2A.

FIGS. 2A and 2B depict another embodiment of an electroplating apparatus 100B including a reference electrode 20 present about a perimeter of the cathode 5, in which a portion of the reference electrode 20 is overlapping a portion of the cathode 5. Similar to the embodiment depicted in FIGS. 1A and 1B the outline of the geometry of the reference electrode 20 may match the outline of the geometry of the cathode 5. In one embodiment, the face of the reference electrode 20 that is contacting the plating electrolyte 1 is offset from the face of the cathode 5 that provides the plating surface 4, wherein the reference electrode 20 has a body that is overlapping a portion of the plating surface 4 of the cathode 5. In one embodiment, the reference electrode 20 is overlapping 1% to 20% of the surface area of the cathode 5. In another embodiment, the reference electrode 20 is overlapping 5% to 15% of the surface area of the cathode 5. It is noted that the above disclosure describing the cathode 5, anode 10, bath 2, plating electrolyte 1, reference electrode 20, power supply 24, control system 25 and measuring system 26 that are described above with reference to embodiments consistent with FIGS. 1A and 1B are equally applicable to the embodiment depicted in FIGS. 2A and 2B.

FIGS. 3A and 3B depict another embodiment of an electroplating apparatus 100C, in which the reference electrode 20 is separated from the holder 6 that connects the cathode 5 to the bath 2 containing the plating electrolyte 1. The reference electrode 20 may be present in the bath 2 between the cathode 5 and the anode 10. In one embodiment, the reference electrode 20 is connected to the bath 2 by a holder 50 similar to the holder 6 that connects the cathode 5 to the bath 2. In some embodiments, the closer the reference electrode 20 is to the cathode 5, the more accurate the reference electrode 20 measures the potential of the cathode 5. In one embodiment, the reference electrode 20 is separated from the cathode 5 by a dimension D1 ranging from 5 mm to 200 mm. In another embodiment, the reference electrode 20 is separated from the cathode 5 by a dimension D1 ranging from 20 mm to 60 mm. It is noted that the above disclosure describing the cathode 5, anode 10, bath 2, plating electrolyte 1, reference electrode 20, power supply 15, control system 25 and measuring system 26 that are described above with reference to embodiments consistent with FIGS. 1A and 1B are equally applicable to the embodiment depicted in FIGS. 3A and 3B.

As depicted in FIGS. 4A and 4B, the electroplating apparatus 100D of the present disclosure may further incorporate a thief electrode 30 in combination with the reference electrode 20. The thief electrode 30 is an auxiliary cathode that is placed to divert to itself some current from portions of the work, which would otherwise receive too high a current density. The thief electrode 30 may have a geometry having an outline corresponding to the geometry of the cathode 5 and the reference electrode 20. In one embodiment, the thief electrode 30 has the geometry of a ring that encircles the cathode 5. The thief electrode 30 may be composed of a solid material and may also be composed of a mesh material. In one embodiment, the thief electrode 30 is present on the holder 6 that is connecting or supporting the cathode 5 in the bath 2 that is containing the plating electrolyte 1. In one embodiment, the thief electrode 30 is present about the perimeter of the reference electrode 20. The thief electrode 30 may have its own power supply 28 (hereafter referred to as thief power supply 28). The negative terminal of the thief power supply 28 may be connected to the thief electrode 30 and the positive terminal of the thief power supply 28 may be connected to the anode 10 of the plating apparatus. It is noted that the above disclosure describing the cathode 5, anode 10, bath 2, plating electrolyte 1, reference electrode 20, power supply 24, control system 25 and measuring system 26 that are described above with reference to embodiments consistent with FIGS. 1A and 1B are equally applicable to the embodiment depicted in FIGS. 4A and 4B.

The electroplating apparatus 100A, 100B, 100C, 100D, depicted in FIGS. 1A-4B may be employed in a plating method, in which a reference electrode 20 is used to measure the potential at the cathode 5 during a controlled-potential method of electroplating. In one embodiment, the electroplating method begins with providing a bath containing a plating electrolyte. A counter electrode is positioned in a first portion of the plating electrolyte and a working electrode is positioned in a second portion of the plating electrolyte. As used herein, the working electrode is the electrode of the plating system at which the metal plating is being deposited. The counter electrode is the electrode having the opposite charge as the working electrode. For example, when the working electrode is connected to the negative terminal of the power supply, the working electrode is the cathode 5 and the counter electrode is the anode 10. Although the examples included herein describe the working electrode as being the cathode 5 and the counter electrode as being the anode 10, embodiments have been contemplated in which the working electrode is the anode 10 and the counter electrode is the cathode 5. A reference electrode 20, as described above with reference to FIGS. 1A-4B, measures the potential of the working electrode. The reference electrode 20 is typically present around the perimeter of the working electrode, e.g., the cathode 5.

In accordance with the present method, a bias is applied to the working electrode, i.e., the cathode 5, and the counter electrode, i.e., the anode 10, to deposit metal from the plating electrolyte 1 onto the working electrode, wherein measurements of the potential by the reference electrode 20 relative to the working electrode are used to determine the bias being applied to the working electrode and the counter electrode.

Potential controlled electroplating is suitable for multiple applications. For example, the electroplating method may be utilized to remove native oxides from the working electrode, e.g., cathode 5, prior to plating the working electrode with metal from the plating electrolyte 1. In another example, the electroplating method may be utilized to plate alloyed compositions, in which compositional control of the alloy is provided by controlling the potential measured with the reference electrode 20.

In one embodiment of an electroplating method that removes natural oxides, a first bias is applied to the anode 10 and the cathode 5 to reduce a metal oxide on the cathode 5. The first bias is applied until a first potential measured at the reference electrode 20 relative to the cathode 5 indicates that the metal oxide at the working electrode has been substantially removed. Examples of materials that can be treated to provide a substantially oxide free surface include Ru, Ni, Co, W, Ta, Mo, Ti, Ag and Au. Thereafter, a second bias is applied the anode 10 and the cathode 5 to deposit the metal ions from the plating electrolyte 1 onto the cathode 5, wherein a second potential created by the second bias is measured by the reference electrode 20 relative to the cathode 5.

In addition to the above described example, embodiments for electroplating methods that remove native oxides from the deposition surface, i.e., plating surface 4 of the cathode 5, prior to depositing the metal plating have been contemplated in which the metal constituent of the metal oxide includes at least one metal selected from the group consisting of Ni, Ta, Ru, W, Cr, Cu, Md and combinations thereof. The metal ion to be plated following removal of the metal oxide to provide a substantially oxide free deposition surface include, but are not limited to, Ni, Al, Ti, Cu, Ni, Co, Fe, Sn, SnAg, Pb, Cr, Au, Pt, or a combination thereof.

In one embodiment of a potential-controlled electroplating method for depositing alloyed compositions, the composition of the alloy being deposited is controlled using the potential measured from the cathode 5 with the reference electrode 20. In this embodiment, the bath 2 containing the plating electrolyte 1 includes a first metal compound and a second metal compound. The potential that provides the correct ratio of the first metal from the first metal compound to the second metal from the second metal compound for the desired alloy to be plated is then determined. The potential for an alloy composition can be determined experimentally from a compositional analysis of platings formed on the cathode 5 from the bath 2 of the plating electrolyte 1 using various measured potentials from the reference electrode 20.

Once the potential for the desired alloy composition is determined, the plating method includes applying a bias to the anode 10 and the cathode 5 to deposit a plating on the cathode 5 having a ratio of the first metal cation from the first metal compound to the second metal cation from the second metal compound. In one embodiment, the composition of the plating being deposited on the cathode 5 is a silver-containing alloy. Examples include SnAg, SnAgCu or SnAgZn.

In this case, the Ag composition can range from 1% to 4% for a given bath composition. The value of the composition is dependent upon the exposed surface area, the aspect ratio of the opening, the diffusion layer thickness, the depth of the deposit, etc. In a traditional plating system, each combination would have to be determined experimentally and monitored each day to determine if the process were stable. However, by utilizing a potential controlled plating operation, the correct composition can be controlled precisely since it is the surface potential that dictates the composition which is influenced by all of the above parameters.

It is noted that the above examples are provided for illustrative purposes and are not intended to limit the invention. It is noted that the present method is not limited to silver containing alloys, as other plating compositions have been contemplated and are within the scope of the present disclosure.

FIGS. 5A-8B depict structures and methods for electroless deposition. Electroless plating, also known as chemical or auto-catalytic plating, is a non-galvanic type of plating method that involves several simultaneous reactions in an aqueous solution, which occur without the use of external electrical power. In one example, the reaction is accomplished when hydrogen is released by a reducing agent, normally sodium hypophosphite (the hydrogen leaves as a hydride ion), and oxidized thus producing a negative charge on the surface of the part. In one example, electroless deposition of nickel is a chemical reduction process that depends upon the catalytic reduction process of nickel ions in an aqueous solution (containing a chemical reducing agent) and the subsequent deposition of nickel metal without the use of electrical energy. In some embodiments, an electroless deposition apparatus is provided in which a reference electrode 20 is positioned in close proximity to the plating surface to measure the potential of the plating surface 3 of the deposition substrate 8 during the deposition process.

FIGS. 5A and 5B depict one embodiment of an electroless deposition apparatus having a reference electrode 21 that is present about the perimeter of the deposition substrate 8. In one embodiment, the electroless deposition apparatus 5A includes a deposition substrate 8 present in a bath 12 including a plating electrolyte 13. A reference electrode 21 is present about a perimeter of the deposition substrate 8. The electroless deposition apparatus 100E further includes a measuring system 40 in electrical communication with the reference electrode 21 to measure the potential of the deposition substrate 8.

The deposition substrate 8 may be composed of any material that can be plated by electroless deposition. For example, the deposition substrate 8 may be composed of a metal, such as steel, brass or aluminum, or a plastic. The deposition substrate 8 may also be composed of semiconductor and glass materials. When plating the surface of a deposition substrate 8 that is not composed of a conductive material, the deposition substrate 8 may need to be catalyzed prior to plating. The catalytic treatment acts to catalyze and/or accelerate the depositing of the metal film on the surface and causes the film to form a continuous and adherent layer. One example of a catalyst for nickel deposition on a plastic deposition substrate 8 is palladium. One technique for catalyzing a deposition substrate is to utilize a plurality of baths in which the deposition substrate 8 is first immersed in a stannous chloride solution followed by immersion in an acidic palladium chloride solution to form an activating deposit of palladium on the deposition substrate 8.

After the immersion of the deposition substrate 8 in the catalyst solution, the deposition substrate 8 is removed from the solution, rinsed free of excess solution and air dried. The deposition substrate 8 is then contacted with the plating electrolyte 13. Such electroless plating electrolytes 13 include baths which will deposit arsenic, chromium, cobalt, cobalt-nickel, copper, gold, iron, nickel and palladium. The baths are usually in the form of basic solution of a salt of the metal to be deposited together with stabilizing agents and a reducing agent, such as sodium hypophosphite.

In one embodiment, in which the electroless deposition process forms a plating composed of Ni, the plating electrolyte 13 is composed of a source of nickel, a reducing agent to supply electrons for the reduction of nickel, energy (heat), complexing agents (chelators) to control the free nickel available in reaction, buffering agents to resist the pH changes caused by the hydrogen generated during deposition, accelerators (exultants) to help increase the speed of the reaction, and inhibitors (stabilizers) to help control reduction.

Examples of reducing agents include sodium hypophophite, aminoboranes, sodium borohydride, and hydrazine. One example of a suitable source for nickel deposition is a hypophosphite reduced electroless nickel plating solution that is composed of at least one of nickel chloride, sodium hypophosphite, ammonium chloride, and sodium citrate. In one embodiment, the sodium citrite may be replaced with ammonium citrate. In another embodiment, the hypophosphite reduced electroless nickel plating solution is composed of nickel chloride, sodium hypophosphite and sodium hydroxyacetate. Another example of a suitable source for nickel deposition is an aminoborane bath or a sodium borohydride bath. The aminoborane bath may include N-dimethylamine borane or H-diethylamine borane. The borohydride bath may include any water soluble borohydride, such as sodium borohydride.

Complexing agents are utilized in the plating electrolyte 13 to control the reaction so that it occurs only on the catalytic surface. Complexing agents suitable for electroless Ni deposition include organic acids and their salts. In electroless deposition of Ni, the complexing agent stabilize the solution and retard the precipitation of nickel phosphite. Complexing agents can reduce the plating rate. An accelerator composed of organic additives may be utilized to increase the rate of deposition. One example of an accelerator that is suitable for hypophosphite reduced solutions for depositing Ni include succinic acid. Other examples of accelerators include carbonic acids and soluble fluorides.

The plating electrolyte 13 may also include at least one inhibitor. Inhibitors control the reduction reaction so that Ni may be deposited at a predictable rate. Inhibitors that are suitable for hypophosphite reduced solutions include sulfur compounds, such as thiourea; oxyanions, such as molybdates or iodates; and heavy metals, such as lead, bismuth, tin or cadmium. Organic sulfide, thio compounds, and metals, such as selenium and thallium, are used to inhibit aminoborane reduced and borohydride reduced electroless nickel solutions.

In one embodiment, in which the electroless deposition process forms a plating composed of Cu, the plating electrolyte 13 contains at least a source of copper and a reducing agent. The source of copper may be a simple cupric salt, such as copper sulfate, copper chloride, or copper nitride. Some examples of reducing agents for plating electrolytes 13 that deposit copper include formaldehyde, dimethylamine borane, borohydride, hypophosphite, hydrazine, sugares, e.g., sucrose, glucose, etc., and dithionite. Complexing agents for plating electrolyte 13 suitable for Cu deposition include tartrate salts; alkanol amines, such as quadrol(N,N,N',N' tetrakis(2-hydroxypropyl)ethylenediamine); and EDTA (ethylenediamine tetraacetic acid).

The plating electrolyte 13 may also be selected to provide Ag and Au platings using an electroless deposition process. The above compositions for the plating electrolyte 13 are provided for illustrative purposes only. It is noted that any plating electrolyte 13 is suitable for the electroless deposition method disclosed herein.

The amount of energy or heat present in the plating electrolyte 13 affects the coating process. In most instances the temperature of the plating electrolyte 13 for electroless deposition ranges from 80° C. to 95° C.

The plating electrolyte 13 for the electroless deposition process is contained within a bath 12. The bath 12 may be any vessel capable of holding a plating electrolyte, i.e., liquid solution. The bath 12 is typically composed of a non-conductive material, i.e., insulating material. Examples of materials for the bath 12 include glass, rubber, plastic or Koroseal™.

Similar to the reference electrode 20 that is described above in reference to the electroplating apparatus and method depicted in FIGS. 1A-4B, the reference electrode 21 for electroless deposition carries essentially no current and is, itself, unpolarized. The reference electrode 21 is present continuously about the perimeter of the deposition substrate 8. In one embodiment, the reference electrode 21 has the same geometric profile as the deposition substrate 8. For example, in the embodiment, in which the deposition substrate 8 is substantially concentric, the reference electrode 21 is substantially concentric. In the embodiment, in which both the deposition substrate 8 and the reference electrode 21 are both concentric, the reference electrode 21 is a circular ring that surrounds the circular deposition substrate 8. The outline of the reference electrode 21 is consistent with the outline of the deposition substrate 8 to ensure that the reference electrode 21 is in close proximity to the deposition substrate 8, but is not in direct contact with the deposition substrate 8. The reference electrode 21 may be connected to the bath 12 that contains the plating electrolyte 13 by a holder 9. The holder 9 is typically composed of the same material as the bath 2. In one embodiment, the reference electrode 21 is separated from the deposition substrate 8 by an insulating material, such as an insulating spacer 11. In one embodiment, the insulating spacer 11 is an integrated component of the holder 9 for the deposition substrate 8.

The reference electrode 21 is separated from the deposition substrate 8 by a radial gap G2. The radial gap G2 may be a dimension separating the deposition substrate 8 from the reference electrode 21 ranging 0.1 mm to 100 mm. In one embodiment, the radial gap G2 may be a dimension separating the deposition substrate 8 from the reference electrode 21 ranging from 1 mm to 10 mm. In another embodiment, the radial gap G2 may be a dimension separating the deposition substrate 8 from the reference electrode 21 ranging from 2 mm to 3 mm.

In one embodiment, the reference electrode 21 has a face 19 that is in contact with the plating electrolyte 1 that is offset from the plating surface 3 of the deposition substrate 8. Although not depicted in FIG. 5A, the reference electrode 21 may have a face in contact with the plating electrolyte that is coplanar with a plating surface of the deposition substrate (not shown).

Several different compositions are suitable for the reference electrode 21. A few examples for the electrode composition of the reference electrode 21 are $Hg/Hg_2Cl_2$ (calomel), $Ag/AgCl$, $Hg/HgSO_4$, or a copper metal electrode ($Cu/Cu^{+2}$ couple). Other examples of suitable materials for the reference electrode 21 include, but are not limited to, Ag, Ni, Fe, Al, platinized Ti, SS 316, SS 304, Mo, W, Ru, Rh, Pd, In, Sn, Ta, Ir, Pt, Pb, Bi, Cr, Au, Zr, Nb and combinations and alloys thereof.

Referring to FIG. 5B, the electroless deposition apparatus 100E further includes a measuring system 40, such as a voltmeter, that is electrically connected to the deposition substrate 8 and the reference electrode 21 to provide a measurement of the potential of the deposition substrate 8. In one example, the measuring system 40 is a voltmeter or potentiostat.

FIGS. 6A and 6B depict another embodiment of an electroplating apparatus 100F including a reference electrode 21 present about a perimeter of the deposition substrate 8, in which a portion of the reference electrode 21 is overlapping a portion of the deposition substrate 8. Similar to the embodiment depicted in FIGS. 5A and 5B, the outline of the geometry of the reference electrode 21 may match the outline of the geometry of the deposition substrate 8. In one embodiment, the face of the reference electrode 21 that is contacting the plating electrolyte 13 is offset from the face of the deposition substrate 8 that provides the plating surface 3, wherein the reference electrode 21 has a body that is overlapping a portion of the plating surface 3 of the deposition substrate 8. In one embodiment, the reference electrode 21 is overlapping 1% to 20% of the surface area of the deposition substrate 8. In another embodiment, the reference electrode 21 is overlapping 5% to 15% of the surface area of the deposition substrate 8. It is noted that the above disclosure describing the deposition substrate 8, bath 12, plating electrolyte 13, reference electrode 21 and measuring system 40 that are described above with reference to embodiments consistent with FIGS. 5A and 5B are equally applicable to the embodiment depicted in FIGS. 6A and 6B.

Figure 7A:
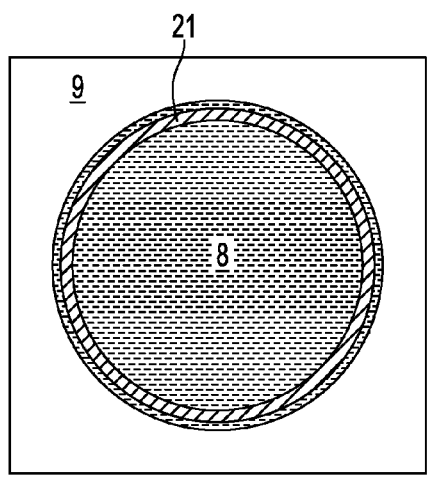
FIG. 7A is a side cross-sectional view of an electroless deposition apparatus in which the reference electrode is separated from the holder of the substrate, in accordance with one embodiment of the present disclosure.
Figure 7B:
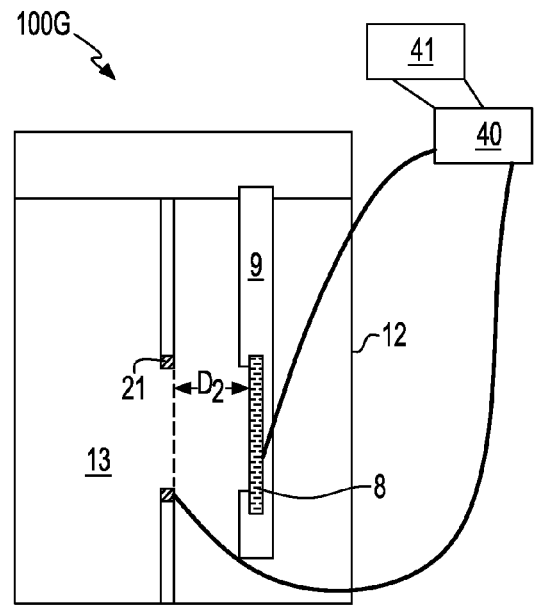
FIG. 7B is a side cross-sectional view of an electroless deposition apparatus including the reference electrode depicted in FIG. 7A.

FIGS. 7A and 7B depict another embodiment of an electroplating apparatus 100G, in which the reference electrode 21 is separated from the holder 9 of the deposition substrate 8. In some embodiments, the closer the reference electrode 21 is to the deposition substrate 8, the more accurate the reference electrode 21 measures the potential of the deposition substrate 8. The geometry of the reference electrode 21 provides an outline that is substantially equal to the perimeter of the deposition substrate 8. In one embodiment, the reference electrode 21 is separated from the deposition substrate 8 by a dimension D2 ranging from 5 mm to 200 mm. In another embodiment, the reference electrode 21 is separated from the deposition substrate 8 by a dimension D2 ranging from 20 mm to 60 mm.

In the embodiment depicted in FIGS. 7A and 7B, the reference electrode 21 has a ring geometry and the deposition substrate 8 is substantially circular. Other embodiments have been contemplated in which the reference electrode 21 and the deposition substrate 8 each have a multi-sided geometry, e.g., rectangular. In the embodiments depicted in FIGS. 7A and 7B, the reference electrode 21 does not overlap the deposition substrate 8. Embodiments have be contemplated, in which a portion of the reference electrode 21 overlaps a portion of the deposition substrate 8 about the deposition substrate's 8 perimeter. In one embodiment, the reference electrode 21 is overlapping 1% to 20% of the surface area of the deposition substrate 8. In another embodiment, the reference electrode 21 is overlapping 5% to 15% of the surface area of the deposition substrate 8. It is noted that the above disclosure describing the deposition substrate 8, bath 12, plating electrolyte 13, reference electrode 21 and measuring system 40 that are described above with reference to embodiments consistent with FIGS. 5A and 5B are equally applicable to the embodiment depicted in FIGS. 7A and 7B.

Figure 8A:
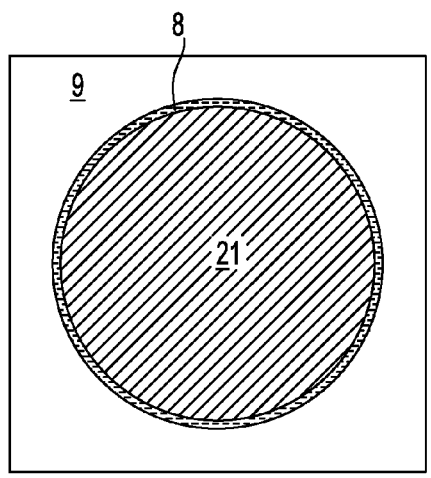
FIG. 8A is a side cross-sectional view of an electroless deposition apparatus in which the reference electrode is separated from the holder of the substrate and is overlapping the entirety of the deposition substrate, in accordance with one embodiment of the present disclosure.
Figure 8B:
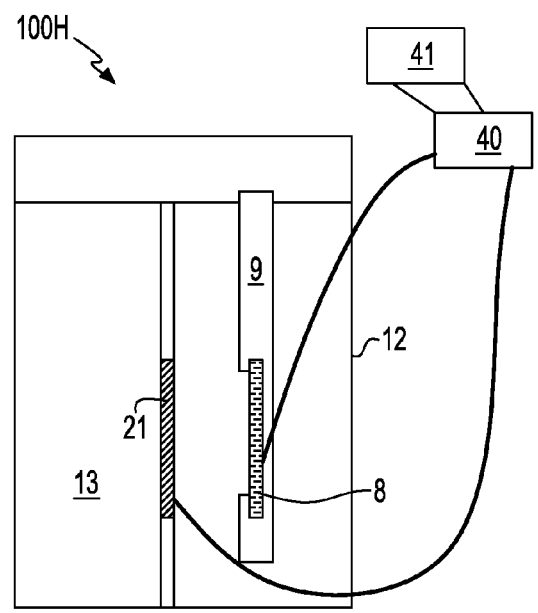
FIG. 8B is a side cross-sectional view of an electroless deposition apparatus including the reference electrode depicted in FIG. 8A.

FIGS. 8A and 8B depict an electroless deposition apparatus 100H in which the reference electrode 21 is separated from the holder 9 of the deposition substrate 8 and is overlapping the entirety of the deposition substrate 8. Although not depicted in FIGS. 8A and 8B, embodiments have also been contemplated in which the reference electrode 21 overlaps the entirety of the deposition substrate 8, and is mounted to the same holder that the deposition substrate 8 is mounted to (The holder identified by reference number 9). In one embodiment, the reference electrode 21 is separated from the deposition substrate 8 by a dimension D3 ranging from 5 mm to 200 mm. In another embodiment, the reference electrode 21 is separated from the deposition substrate 8 by a dimension D3 ranging from 20 mm to 60 mm. The above disclosure describing the deposition substrate 8, bath 12, plating electrolyte 13, reference electrode 21 and measuring system 40 with reference to embodiments consistent with FIGS. 5A and 5B are equally applicable to the embodiments depicted in FIGS. 8A and 8B.

The electroless deposition apparatus 100E, 100F, 100G, 100H depicted in FIGS. 5A-8B may be employed in a plating method, in which a reference electrode 21 is used to measure the potential at the deposition surface 8 during an electroless deposition process. In this embodiment, the measured potential of the deposition surface 8 provides the criterion for end point detection. End point detection is a measurement of the completion of the plating on the deposition surface 8, and hence the termination of the electroless deposition process.

In one embodiment, the electroless deposition method begins with providing a bath 12 containing a plating electrolyte 13 having at least one metal compound. A reference electrode 21 is then positioned about the perimeter of a deposition substrate 8. The reference electrode 21 measures the potential of the deposition substrate 8. The deposition substrate 8 and the reference electrode 2 are positioned in the plating electrolyte 13 to plate the deposition substrate 8 with a metal from the at least one metal compound of the plating electrode 13. To increase the plating rate the plating electrolyte 13 may be heated. The potential of the deposition substrate 8 is measured using the reference electrode 21.

The duration of the electroless deposition is determined using a potential based end point detection method. By "potential based" it is meant that the potential at the deposition substrate 8 is measured using the reference electrode 21 and when a reference potential is reached the electroless deposition process is terminated. The reference potential may be the open circuit potential for the plating composition on the deposition substrate. The "open circuit potential" is the difference of electrical potential between two terminals, i.e., the reference electrode 21 and the deposition substrate 8, when there is no external load connected. In one example, the open circuit potential may range 300 mV to 200 mV.

The electroless deposition apparatuses 100E, 100F, 100G, 100H depicted in FIGS. 5A-8B may also be employed in an etch method, in which a reference electrode 21 is used to measure the potential at the surface being etched during an electroless etch process. In this embodiment, the measured potential of the etch surface provides the criterion for end point detection. The etch substrate may be positioned relative to the electrolyte similar to the manner in which the deposition substrate 8 of the electroless deposition apparatus is position relative to the plating electrolyte 13, as described with reference to FIGS. 5A-8B.

In one example, the electroless etch method begins with providing a bath including an electrolyte. Examples of electrolyte baths suitable for electroless etching include, but are not limited to ammonium persulfate, $H_2O_2$/acetic acid, 10% $HNO_3$ and combinations thereof.

A reference electrode is then positioned about the perimeter of the etch substrate to measures a potential of the etch substrate. The reference electrode 21 that is described above in the electroless deposition apparatuses depicted in FIGS. 5A-9B is suitable for application in the electroless etch process.

The etch substrate and the reference electrode may be positioned in the electrolyte, and an oxidizing reaction removes at least one metal from the etch substrate. For example, an electrolyte composed of ammonium persulfate is suitable for removing a metal, such as Cu, from the etch substrate.

The potential of the etch substrate is measured using the reference electrode while the etch substrate is submerged in the electrolyte. The etch substrate is removed from the bath when the potential of the etch substrate is equal to an open circuit potential.

While the invention has been particularly shown and described with respect to preferred embodiments thereof, it will be understood by those skilled in the art that the foregoing and other changes in form and details may be made therein without departing from the spirit and scope of the present invention.

What is claimed is:

1. A plating method comprising:
    providing a bath containing a plating electrolyte;
    providing a counter electrode in a first portion of the bath;
    providing a working electrode in a second portion of the bath, wherein the working electrode is circular;
    providing a reference electrode in the bath to measure the potential of the working electrode, wherein the reference electrode is present around a perimeter of the working electrode and is separated from the working electrode by an insulating spacer, and wherein the reference electrode is a circular ring surrounding the working electrode and has a face that is in contact with the plating electrolyte offset from a plating surface of the working electrode; and
    applying a bias to the working electrode and the counter electrode to deposit metal from the plating electrolyte on the working electrode, wherein measurements of the potential of the reference electrode relative to the working electrode are used to determine the bias being applied to the working electrode and the counter electrode.

2. The method of claim 1, wherein a portion of the reference electrode is overlapping a portion of the working electrode.

3. The plating method of claim 1 further comprising:
applying a first bias to the counter electrode and the working electrode to reduce a metal oxide on the working electrode, wherein the first bias is applied until a first potential measured at the reference electrode relative to the working electrode indicates that the metal oxide at the working electrode has been substantially removed; and
applying a second bias to the counter electrode and the working electrode to deposit the metal from the plating electrolyte on the working electrode, wherein a second potential created by the second bias is measured by the reference electrode relative to the working electrode.

4. The method of claim 3, wherein the metal oxide comprises a metal selected from the group consisting of Ni, Al, Ti, Ta, Ru, W, Cr, Cu, Md or a combination thereof.

5. The plating method of claim 1, wherein the bath containing the plating electrolyte includes a first metal compound and a second metal compound and the plating method further comprising applying the bias to the counter electrode and the working electrode to provide a potential measured by the reference electrode to deposit a plating having a ratio of the first metal cation from the first metal compound to the second metal cation from the second metal compound.

6. The electroplating method of claim 5, wherein an alloy comprised of the first metal cation and the second metal cation is comprised of SnAg, SnAgCu, SnAgZn or combinations thereof.

7. The method of claim 1, wherein the working electrode is separated from the reference electrode by a radial gap.

8. The method of claim 7, wherein the radial gap ranges from 0.1 mm to 100 mm.

9. An electroless deposition method comprising:
providing a bath including a plating electrolyte;
positioning a reference electrode about a perimeter of a deposition substrate, wherein the reference electrode is separated from the deposition substrate by an insulting spacer, and wherein the reference electrode measures a potential of the deposition substrate;
positioning the deposition substrate and the reference electrode in the plating electrolyte to plate the deposition substrate with a metal from the at least one metal compound of the plating electrolyte; and
measuring the potential of the deposition substrate using the reference electrode, wherein the deposition substrate is removed from the bath when the potential of the coating substrate is equal to the open circuit potential for a plating composition on the deposition substrate,
wherein the deposition substrate is circular, and the reference electrode is a circular ring surrounding the deposition substrate, and wherein the reference electrode has a face that is in contact with the plating electrolyte offset from a plating surface of the deposition substrate.

10. The method of claim 9, wherein a portion of the reference electrode is overlapping a portion of the deposition substrate.

11. The method of claim 9, wherein the reference electrode is separated from the deposition substrate by a radial gap.

12. The method of claim 11, wherein the radial gap ranges from 0.1 mm to 100 mm.

13. An electroless etch method comprising:
providing a bath including an electrolyte;
positioning a reference electrode about a perimeter of an etch substrate, wherein the reference electrode is separated from the etch substrate by an insulting spacer, and wherein the reference electrode measures a potential of the etch substrate;
positioning the etch substrate and the reference electrode in the electrolyte in which an oxidizing reaction removes at least one metal from the etch substrate; and
measuring the potential of the etch substrate using the reference electrode, wherein the etch substrate is removed from the bath when the potential of the etch substrate is equal to an open circuit potential.

14. The method of claim 13, wherein the etch substrate is circular, and the reference electrode is a circular ring surrounding the working electrode.

15. The method of claim 14, wherein the etch substrate is separated from the reference electrode by a radial gap.

16. The method of claim 14, wherein a portion of the reference electrode is overlapping a portion of the etch substrate.

* * * * *